US00PP18108P3

(12) United States Plant Patent
Stemkens

(10) Patent No.: US PP18,108 P3
(45) Date of Patent: Oct. 2, 2007

(54) ***NEMESIA* PLANT NAMED 'NEMHAPRI'**

(50) Latin Name: ***Nemesia* hybrid**
Varietal Denomination: Nemhapri

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/301,090

(22) Filed: Dec. 12, 2005

(65) Prior Publication Data

US 2007/0136910 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—Bruce Vrana

(57) ABSTRACT

A new and distinct variety of *Nemesia* plant, substantially as herein illustrated and described, characterized particularly as to novelty by a semi-trailing and compact habit, big pink and orange flowers, very early flowering and absolutely no seed set.

1 Drawing Sheet

Latin name of the genus and species of the plant claimed: *Nemesia* hybrid.

Varietal denomination: 'Nemhapri'.

BACKGROUND OF THE NEW PLANT

The present invention relates to a new and distinct cultivar of *Nemesia* plant known botanically as *Nemesia* hybrid and that will be referred to hereinafter by the cultivar name 'Nemhapri.'

The new *Nemesia* is a product of a planned breeding program conducted by the inventor in Enkhuizen, The Netherlands. The goals of the breeding program were to improve on plant habit by breeding plants that were more compact and basal branching. Earliness of flowering was another character that was very important in the breeding process, together with producing no seed pods.

The new *Nemesia* originated from a cross-pollination made by the inventor in 2002 of an unpatented *Nemesia* plant, named 'D0366-2,' as the female, or seed, parent with an unpatented *Nemesia* plant named 'E0131-6,' as the male, or pollen, parent. The cultivar 'Nemhapri' was discovered and selected by the Inventor as a plant within the progeny from this cross-pollination in a controlled environment in Enkhuizen, The Netherlands, in 2003.

As a result of this cross the present cultivar was created in 2003 in Enkhuizen, Netherlands and has been repeatedly asexually reproduced by cuttings in Enkhuizen, Netherlands and Sarrians, France over a two year period. It has been found to retain its distinctive characteristics through successive propagations. The new variety is stable and reproduces true to type in successive generations of asexual reproduction.

DESCRIPTION OF THE DRAWING

This new *Nemesia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Nemesia*. The data which defines these characteristics were collected from asexual reproductions carried out in Enkhuizen, Netherlands. The plant history was taken on 14 weeks old plants, blossomed under natural light in a greenhouse, and grown in a 10.5 cm container.

Color readings were taken in the greenhouse under ambient light. Color references are primarily to The R.H.S. Colour Chart of The Royal Horticultural Society of London.

TABLE 1

Differences between the new cultivar 'Nemhapri', its parents and a similar cultivar

| | 'Nemhapri' | 'D0366-2' | 'E0131-6' | 'Sunsatia blackberry' |
|---|---|---|---|---|
| Seed set | No | No | Plentiful | Medium |
| Flower size | 2.9 cm long, 3.2 cm wide | 1.4 cm long, 1.6 cm wide | 2.9 cm long, 3.2 cm wide | 1.4 cm long, 1.6 cm wide |
| Flower color | Pink-orange | White | Orange | Rose |

The commercial name of the most resembling variety is 'Sunsatia blackberry.' This variety is not patented.

The plant:

*Classification.*—Botanical: *Nemesia.*

*Parentage.*—Female parent: Seedling named 'D0366-2' is one of our seedlings from our D-generation of plants bred in 2002. Pollen parent: A seedling named 'E0131-6' is one of our seedlings from our E-generation of plants bred in 2003.

*Growth habit.*—Semi-trailing and compact.

*Plant height.*—18–26 cm.

*Speading area of plant.*—16–28 cm.

*Temperature tolerance.*—Plants of the new *Nemesia* have been observed to tolerate temperatures from −2 to 38 degrees C.

*Branching character.*—Freely branching and lateral branching at every node.

*Number of branches per plant.*—30–60.

*Blooming period.*—From April until November.

*Propagation.*—Vegetative stem cuttings.

*Sexuality.*—Hermaphrodite.

*Time to initiate roots.*—Approximately 10 days at temperatures of 21 degrees centigrade is needed to produce cuttings.

*Root system.*—Numerous and fine, the color is N155A.

The stem:

*Diameter.*—4–5 mm.

*Length.*—14–16 cm.

*Shape.*—Quadrilateral with ridges.

*Anthocyan pigmentation.*—Absent.

*Color of the stem.*—137A.

*Length of internode.*—14–20 mm.

*Pubescence.*—Glabrous.

*Length lateral branches.*—10–12 cm.

The foliage:

*Phyllotaxis.*—Opposite.

*Shape of blade.*—Broadly ovate.

*Attachment.*—Petiolate.

*Texture.*—Upper side: Glabrous. Lower side: Glabrous.

*Venation.*—Pinnate.

*Leaf margin.*—Crenate.

*Leaf base.*—Truncate.

*Leaf apex.*—Apiculate.

*Length.*—20–60 mm.

*Width.*—15–40 mm.

*Depth of incision.*—Less than 1 mm.

*Color.*—Upper side: 141B. Lower side: 138B.

*Petiole length.*—1–2 mm.

*Petiole surface structure.*—Glabrous.

*Petiole diameter.*—2–3 mm.

*Petiole coloration.*—Upper side: 141B. Lower side: 138A.

The bud:

*Peduncle length.*—10–20 mm.

Peduncle diameter.—2–3 mm.

*Peduncle color.*—141B.

*Peduncle surface.*—Glabrous.

*Pedicel length.*—4–12 mm.

*Pedicel diameter.*—Less than 1 mm.

*Pedicel color.*—141B.

*Stipule length.*—1–2 mm.

*Stipule width.*—1–2 mm.

*Stipule shape.*—Lanceolate.

*Stipule color.*—Upper side: 141B. Lower side: 141C.

*Bud size.*—Diameter: 4 mm. Length: 3–5 mm.

*Bud shape.*—Globular.

*Bud color.*—N155B.

*Bud surface.*—Glabrous.

*Sepals.*—Color (Upper side): 137B. Color (Lower side): 137B. Form: Upright. Surface: Glabrous. Number: 5, fused. Length: 1–2 mm. Width: Less than 1 mm. Shape: Lanceolate. Apex: Apiculate. Base: Fused. Margin: Entire.

The flower:

*Type of inflorescence.*—Axillary raceme.

*Flower shape.*—Personate.

*Palate color.*—N25B.

*Nectary (located on the under side of palate).*—4 mm in width and 4 mm in length.

*Nectary color.*—N186C.

*Throat color (upper surface).*—158B.

*Throat color (lower surface).*—157C.

*Surface of upper lip.*—Upper side: Glabrous. Lower side: Glabrous.

*Surface of lower lip.*—Upper side: Glabrous. Lower side: Glabrous.

*Lip margin (lower lip).*—Entire.

*Lip margin (upper lip).*—Entire.

*Number of lips.*—2.

*Lobes.*—Upper lip: 4. Lower lip: 1.

*Lobes on upper lip fused or unfused.*—Fused.

*Lip apex (upper lip).*—Each lobe has a rounded apex.

*Lip base (upper lip).*—Fused.

*Lip apex (lower lip).*—Obtuse.

*Lip base (lower lip).*—Fused.

*Upper lip color.*—Upper side: 48C with venation 48B and an indentation of N186C. Lower side: 52B with venation 52A.

*Lower lip color.*—Upper side: 22A with venation N25C. Lower side: 52B with venation 52A.

*Flower dimensions.*—1.3 cm in depth, 2.9 cm in length and 3.2 cm in width at the widest part.

*Lower lip dimensions.*—1.4 cm in length and 2.8 cm in width.

*Upper lip dimensions.*—1.5 cm in length and 3.2 cm in width.

*Lobe dimensions (upper lip).*—1.3 cm in length and 8 mm in width.

*Flower spur dimensions.*—0.1 cm in length and 1–2 mm in diameter.

*Spur color.*—158B.

*Calyx dimensions.*—4 mm in length and 5 mm in width.

*Calyx color.*—141C.

*No. of flowers per inflorescence.*—30–50.

*Fragrance.*—No fragrance.

*Bloom time of one inflorescence.*—New florets continue to open in one inflorescence over a period of 35 days.

*Lastingness of a single flower.*—3–7 days.

The reproductive organs:

*Androecium.*—Stamens quantity: 4. Anther shape: ovoid. Anther length: 0.3 mm. Anther width: 0.2 mm. Anther color: 154D. Pollen amount: scarce pollen. Pollen color: 154D.

*Gynoecium.*—Pistils quantity: 1. Pistil length: 3–5 mm. Stigma color: 144C. Style length: 3–5 mm. Style color: 144D. Ovary color: 144C. Ovary position: Superior. Ovary shape Oval. Ovary dimensions: 0.3 mm in width and 0.4 mm in length.

Seeds: No seed set is observed. No fruits are formed.

Disease and pest susceptibility or resistance: There are no disease problems known to the inventor other than what effect typical *Nemesia*.

What is claimed is:

1. A new and distinct cultivar of *Nemesia* plant named 'Nemhapri,' as substantially illustrated and described herein.

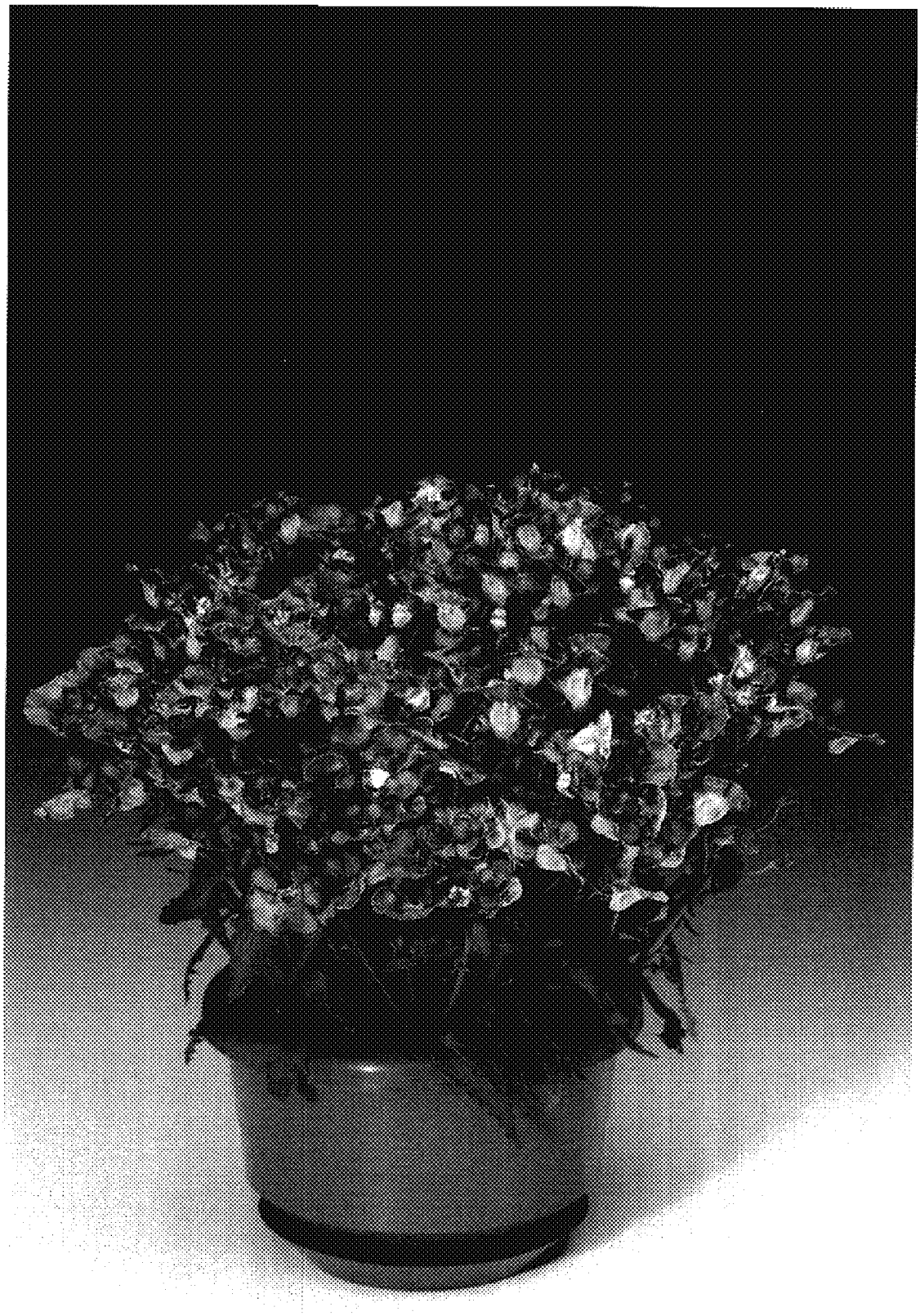

* * * * *